United States Patent [19]

Green et al.

[11] 4,188,293
[45] Feb. 12, 1980

[54] METHOD OF EFFECTING FLOCCULATION

[75] Inventors: Harold A. Green, Havertown, Pa.;
John J. Merianos, Jersey City;
Alfonso N. Petrocci, Glen Rock, both of N.J.

[73] Assignee: Kewanee Industries, Inc., Bryn Mawr, Pa.

[21] Appl. No.: 980

[22] Filed: Jan. 4, 1979

Related U.S. Application Data

[60] Division of Ser. No. 902,894, May 4, 1978, which is a continuation-in-part of Ser. No. 744,617, Nov. 24, 1976, Pat. No. 4,089,977.

[51] Int. Cl.$^2$ .......................... B01D 21/01; C02B 1/20
[52] U.S. Cl. ........................................ 210/47; 210/43; 210/54; 252/358
[58] Field of Search .................. 209/5; 210/42 R, 47, 210/51–54; 252/180, 358; 260/567.6 H, 567.6 P; 424/329

[56] References Cited

U.S. PATENT DOCUMENTS

| | | | |
|---|---|---|---|
| 3,299,138 | 1/1967 | Sveum et al. | 210/54 |
| 3,334,138 | 8/1967 | Feeman | 260/567.6 P |
| 3,769,346 | 10/1973 | Boissier et al. | 260/567.6 P |
| 3,920,546 | 11/1975 | Newkirk | 210/54 |
| 4,089,780 | 5/1978 | Svarz et al. | 210/54 |
| 4,089,977 | 5/1978 | Green et al. | 424/329 |

Primary Examiner—Charles N. Hart
Assistant Examiner—Peter A. Hruskoci
Attorney, Agent, or Firm—Arthur A. Jacobs

[57] ABSTRACT

A method of effecting flocculation in aqueous systems which comprises applying to said systems an effective amount of a compound or mixture of compounds having the formula:

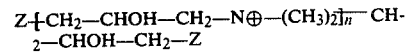

in which Z is either X or —N(CH$_3$)$_2$; is a halogen having an atomic weight greater than 34; and n is an integer of from 2 to 20.

1 Claim, No Drawings

METHOD OF EFFECTING FLOCCULATION

This application is a division of application Ser. No. 902,894, filed May 4, 1978, which was, in turn, a continuation-in-part of application Ser. No. 744,617, filed Nov. 24, 1976 now U.S. Pat. No. 4,089,977.

In the aforesaid application, it was disclosed that compounds, or mixtures of compounds of formula

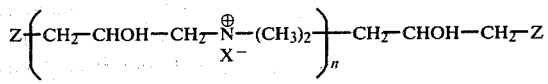

are non-foaming, anti-microbial agents. In the above formula Z is selected from the group consisting of X and $-N(CH_3)_2$, where $X^-$ is an anionic halogen having an atomic weight greater than 34, there being one such anionic halogen for each cationic nitrogen within the bracket, and n is an integer of from 2 to 20.

The aforesaid application also disclosed a method of making compounds of formula shown above, in examples 1, 2, and 3. The disclosures are made part of this application by reference.

It has now been discovered that the compounds of the above formula, or mixtures of such compounds, have several other surprising properties. They are, for example, uniquely excellent hair conditioners that are compatible with a large number of cleansing and lathering surfactants ordinarily used in making shampoos.

Although many hair conditioning agents are available in commerce, many of them are subject to one or more disadvantages. For example, some of them are not sufficiently soluble in water in the presence of relatively high concentrations of surfactants. Also many of them are not sufficiently substantive to hair so that the effect of conditioning is not sustained. In addition, many of them flake off from the hair after the hair is dried because of excessive build up.

In accordance with the present invention it has now been discovered that the compounds of this invention are compatible with most of the surfactants used in shampoo or hair cream formulations even when such surfactants are present in relatively high concentrations.

It has, furthermore, been found that the material of this invention is substantive to the hair for long periods of time, and, when applied to the hair in shampoos, or in cream rinses, it imparts a smooth feeling to the hair. It promotes detangling of the hair and facilitates combing by diminishing "drag". But equally as important, there is no noticeable build up of material on the hair, followed by "flaking off" even after a large number of successive rinsings and shampooings, as is the case with many hair conditioning agents, especially those which are water-insoluble, high molecular weight polymers.

These surprising hair care properties of the compounds of this invention were discovered by testing them on DeMeo hair tresses in a manner well known in the art.

Another unique and novel use for the compounds of this invention, or mixtures of such compounds, is for flocculation in aqueous systems. As flocculants, they cause the sedimentation of some materials which might otherwise remain in aqueous suspension; or, at least, they increase the rate of sedimentation in many cases where continued suspension of such immiscible materials cause a problem when it is desired to clarify and draw off the clear supernatant aqueous solutions, or when it is desired to filter or drain suspensions in industries that require large volumes of water.

The testing of the compounds of this invention for flocculant properties was conducted as follows:

An aqueous suspension was made of bentonite to contain 300 p.p.m. of the solid. The pH was adjusted to either 7 or 3.2 and an aqueous solution or suspension of the present compound or compounds was added to achieve a concentration of 0.1 ppm., and the mixture stirred gently.

If no floc appeared, then additional polymeric material was added to achieve a concentration of 1 ppm., and the mixture stirred gently and observed for the appearance of floc.

In such a manner, the concentration of the present compounds being tested was increased tenfold again and again until such time as flocs appeared. The concentration of polyquaternary ammonium compounds necessary to produce flocs was noted.

This procedure was performed at pH 7, and pH 3.2.

It was found that the ppms of the above suspensions were as follows:

pH 7—All compounds between about 4 ppm. and about 6 ppm.

pH 3.2—All compounds between about 2 ppm. and about 5.5 ppm.

The present compounds may also be used to clarify waters in which the pollutants are emulsified. In such cases, the compounds may cause the emulsion to break.

The ability of the present compounds to de-emulsify is shown by their action on a synthetic, but common type, of oil-in-water emulsion.

The synthetic emulsion was prepared according to the following formula by the usual methods common to the art:

| Components | Parts by Wt. |
| --- | --- |
| Mineral oil | 15.0 |
| Cetyl Alcohol | 1.0 |
| Lanolin | 1.0 |
| "Ammonyx SO" | 2.5 |
| "BTC 2125 M" | 1.0 |
| Water | 79.5 |
|  | 100.0 |

"Ammonyx SO" is the proprietary name for an Amine oxide, and "BTC 2125 M" is the proprietary name for a quaternary ammonium chloride. Both materials are available from Onyx Chemical Co., Jersey City, N.J.

EXAMPLE 1

10 ml. of the oil-in-water emulsion was placed in each of four 1-liter graduates, diluted with distilled water to the mark, and stoppered. The cylinders were inverted several times to disperse the emulsion evenly. To each of two of the cylinders, enough bentonite dispersion was added to make the concentration 100 ppm. The composition was then mixed thoroughly.

One of the dispersions without bentonite and one of the dispersions with bentonite was adjusted to pH 7. To each of these two cylinders there was added a solution of a polyquaternary ammonium compound embodying the present invention to bring its concentration to 100 ppm. Each cylinder was then inverted several times to assure even dispersion and were then set aside to await the appearance of floc. The cylinder with the bentonite produced large flocs which rose to the surface almost immediately. The cylinder without the bentonite produced flocs after about 10 minutes.

The above test was repeated with the two remaining cylinders, one with bentonite the other without bentonite, at pH 3.2. The cylinder with the bentonite produced large flocs almost immediately, while the cylinder without the bentonite produced flocs after 10 to 15 minutes.

The polyquaternary ammonium compound used in each of the above tests was a compound formed by the reaction of equimolar proportions of 1,3-bis-dimethylamino-2-propanol and 1,3-dichloro-2-propanal at a temperature of between about 40° to about 90° C. for about 2 to 12 hours, as set forth in the aforementioned parent application Ser. No. 744,617 now Pat. No 4,089,977, all of which is incorporated herein by reference.

The invention claimed is:

1. A method of effecting flocculation in aqueous systems containing solid particles in suspension which comprises applying to said aqueous systems an effective amount sufficient to form flocs from said solid particles of a compound or mixture of compounds having the formula:

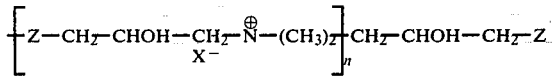

wherein Z is selected from the group consisting of X and $-N(CH_3)_2$, wherein X is a halogen having an atomic weight greater than 34, wherein $X^-$ is the anionic form of X, there being one such anionic halogen for each cationic nitrogen, and wherein n is an integer of from 2 to 20, said compound or mixture of compounds being formed by the reaction of substantially equimolar proportions of 1, 3-bis-dimethylamino-2-propanol and 1, 3-dichloro-2-propanol, the reaction being effected at a temperature of about 40° to about 90° C. for about 2 to 12 hours.

* * * * *